United States Patent [19]  [11] Patent Number: 5,011,988
Thunberg  [45] Date of Patent: Apr. 30, 1991

[54] RECOVERY OF IDA AND GLAUBER'S SALT FROM WASTE CRYSTAL LIQUORS

[75] Inventor: Jon C. Thunberg, Milford, N.H.

[73] Assignee: W. R. Grace & Co.-Conn., Conn.

[21] Appl. No.: 419,920

[22] Filed: Oct. 11, 1989

[51] Int. Cl.$^5$ .......................................... C07C 227/42
[52] U.S. Cl. ................................................ 562/554
[58] Field of Search ............................ 562/554, 572

[56] References Cited

U.S. PATENT DOCUMENTS

| | | | |
|---|---|---|---|
| 3,510,515 | 5/1970 | Colburn | 260/534 |
| 3,808,269 | 4/1974 | Bragdon et al. | 260/534 |
| 3,852,344 | 12/1974 | Bragdon et al. | 260/534 |
| 3,904,585 | 9/1975 | Thunberg et al. | 260/534 |
| 3,974,496 | 3/1976 | Thunberg et al. | 260/534 |
| 4,299,978 | 11/1981 | Nakayasu et al. | 562/554 |
| 4,691,054 | 9/1987 | Tosa et al. | 562/554 |
| 4,818,409 | 4/1989 | Puetter | 210/638 |

FOREIGN PATENT DOCUMENTS 1472840  9/1975  United Kingdom ............... 562/554

Primary Examiner—James H. Reamer
Attorney, Agent, or Firm—Kevin S. Lemack; William L. Baker

[57] ABSTRACT

The separation and recovery of iminodiacetic acid and sodium sulfate decahydrate from sodium sulfate solutions such as the liquor generated in the production of iminodiacetic acids are disclosed. The separation is accomplished by adjusting the temperature of the sodium sulfate solutions to crystallize the iminodiacetic acid and sodium sulfate decahydrate. Nitrilotriacetic acid optionally can be isolated prior to the crystallization of the IDA and sodium sulfate decahydrate.

54 Claims, No Drawings

RECOVERY OF IDA AND GLAUBER'S SALT FROM WASTE CRYSTAL LIQUORS

BACKGROUND OF THE INVENTION

1. Field of the Invention

This invention relates to the recovery of iminodiacetic acid and Glauber's Salt ($Na_2SO_4 \cdot 10H_2O$) from sodium sulfate solutions such as the liquor generated in the process of producing iminodiacetic acid.

2. Description of the Prior Art

Typical prior art processes for the recovery of iminodiacetic acid from sodium sulfate solutions are disclosed in U.S. Pat. Nos. 3,808,269 and 4,299,978.

U.S. Pat. No. 3,808,269, the disclosure of which is herein incorporated by reference, discloses a process of recovering iminodiacetic acid (IDA) from a starting aqueous solution of sodium sulfate and the amino acid having a temperature above about 33° C. and containing at least 5% amino acid. The process comprises adjusting the pH of the starting solution to 1.5–3 to form an IDA precipitate and a first mother liquor; separating the IDA precipitate from the first mother liquor; and recovering the separated IDA. Sodium sulfate can then be precipitated from the first mother liquor by adjusting the temperature so as to prevent precipitation of IDA.

U.S. Pat. No. 4,299,978, the disclosure of which is herein incorporated by reference, discloses a process for separating an "iminodiacetic acid component" from an aqueous glycine solution including IDA. The process comprises adding sulfuric acid in the presence of a sodium salt to the aqueous solution so as to lower the pH to 1.5 or less, whereby an "iminodiacetic acid component" is crystallized from the solution, and separating the precipitated IDA component. Glycine can thus be efficiently recovered with minimal levels of IDA. Glauber's salt is not generated.

The foregoing references use processes where the precipitation of sodium sulfate with the amino acid is avoided. These processes generate waste liquor streams which include a substantial amount of product. Streams such as this have heretofore been discarded.

Other approaches to the recovery of amino acids include U.S. Pat. No. 3,510,575 where glycine is separated from $NH_4Cl$, and U.S. Pat. No. 4,691,054 where amino acids are isolated by ion exchange from systems that are substantially free of inorganic ions (such as sodium sulfate).

SUMMARY OF THE INVENTION

The problems of the prior art have been overcome by the present invention which provides a process for separating IDA and Glauber's Salt from amino carboxylate containing solutions such as the waste liquors generated from the production of IDA.

It is therefore an object of the present invention to provide a process to minimize generation of waste from the production of IDA.

It is a further object of the present invention to provide a process for the recovery of value from the waste generated from the production of IDA.

It is a still further object of the present invention to provide a process which reduces disposal costs in the production of IDA.

According to the present invention, these and other objects which will become more apparent, are accomplished by providing a process for separating and recovering IDA and sodium sulfate decahydrate from a liquor containing IDA and sodium sulfate, which entails forming a slurry of precipitated IDA, sodium sulfate decahydrate and mother liquor by, for example, adjusting the temperature of the liquor to a level sufficient to crystallize the IDA and Glauber's Salt, followed by separation of the mixed crystals from the mother liquor. The mixed crystals can be recycled to a point in the IDA Production process. NTA optionally can be isolated prior to crystallizing the IDA and Glauber's Salt.

DETAILED DESCRIPTION OF THE PREFERRED EMBODIMENTS

The process of preparing IDA from the corresponding nitrile can be accomplished according to the following sequence of reactions:

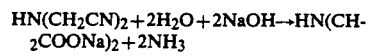

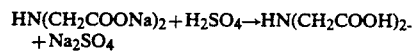

Much of the amino acid now sent to waste in the IDA purge liquor from IDA production processes can be recovered, and optionally recycled, in the process of the present invention. This can be accomplished either batchwise or in a continuous process by forming a slurry comprising precipitated IDA and sodium sulfate decahydrate, and mother liquor. In one example of the batch process, aqueous solutions containing IDA and sodium sulfate, such as waste liquor and recycled liquor produced in the process for the production of IDA, are charged to a cooling crystallizer. The mixture is cooled to a temperature effective for precipitating the amino acid and Glauber's Salt. IDA seed crystals can be added at about the saturation temperature of IDA in the solution. Glauber's Salt seed crystals can be added at about the saturation temperature of sodium sulfate decahydrate in the solution. The solid, which is a mixed wet cake comprising IDA and Glauber's Salt, is separated from the mother liquor by, for example, centrifugation. The solid can be recycled to an earlier point in the production process. A portion of the mother liquor (e.g., 50%) can be recycled to the crystallizer, to reduce the slurry density, for example.

In a second embodiment of the batch process, NTA is isolated prior to the cooling crystallization of IDA and sodium sulfate decahydrate. Thus, a two step crystallization is used; first, acidification followed by crystallization and separation of NTA from the resulting slurry comprising NTA and mother liquor, and second, neutralization back to about the original pH followed by forming a slurry comprising precipitated IDA and sodium sulfate decahydrate, then separation of the resulting crystals. The NTA crystallization can be accomplished by lowering the pH of the solution from about 2.6 to about 2.1 with, for example, sulfuric acid, to decrease the solubility of NTA. NTA seed crystals can be added to stimulate NTA crystallization. A typical starting solution obtained from the production process of IDA has a composition of about 2.9% NTA, 6.3% IDA and 22.6% $Na_2SO_4$. The saturation temperature of NTA in such a solution after acidification to about pH 2.1 is greater than 40° C. Sodium sulfate decahydrate precipitates from the mother liquor after NTA separation and after neutralization with, for example, sodium hydroxide back to a pH of about 2.6, at a temperature of about 27° C. The mother liquor can be cooled to a temperature of about 5° C.

In another embodiment, a continuous crystallization can be used. A slurry of IDA, Glauber's Salt and liquor is prepared at the operating temperature (e.g., about 5° C.). Fresh waste liquor is fed into the stirring slurry while cooling to maintain the operating temperature. The preferred residence time is about 2 hours. Both the IDA and Glauber's Salt crystallize since the crystallizer operates at a temperature below the saturation temperature of both. Slurry is constantly withdrawn and subjected to separation. A portion of the liquor can be returned to the crystallizer.

Separation is preferably accomplished by centrifugation, although other forms of separation such as filtration or decantation could be used. Suitable centrifuges include the traditional vertical perforated bowl centrifuge, which provides excellent separation of entrained liquor. A speed setting corresponding to a centrifugal force of about 500 g–1000 g can be used, with a force of 900–1000 g being most preferable.

In the IDA production process, wash water can be used to wash the cake generated in the IDA production step free of sodium sulfate. However, this wash causes some of the IDA in the cake to redissolve. Further, this water dilutes the liquor. By excluding the wash water, this redissolution and dilution are minimized.

The temperature at which the IDA and Glauber's Salt are precipitated is a function of the concentration of the amino acid and the sodium sulfate in the solution. The typical waste purge stream from the process for the production of IDA has a composition of about 6% IDA and about 23% sodium sulfate. The preferred temperature to which such a solution should be cooled is about 5° C. Those skilled in the art will be able to determine the necessary temperature to which the particular stream must be cooled to precipitate IDA and Glauber's Salt. Separation of precipitate can be carried out at more than one temperature during the cooling, to maintain a workable slurry density, for example. The resulting liquor can be recycled to the crystallizer.

An IDA stream having the aforementioned composition precipitates because of the decreased solubility at about 5° C. as compared to its solubility in the starting solution having a temperature of about 40° C. Simultaneously, solvent (i.e., water) is being removed as $Na_2SO_4$ crystallizes as $Na_2SO_4.10H_2O$. Because this water becomes part of the solids in the slurry, the slurry density becomes high. In the continuous system, the slurry density can be adjusted appropriately by continuously recycling saturated 5° C. mother liquor back to the crystallizer.

The recovered solid, which is a mixture of IDA, Glauber's salt and some entrained liquor, can be recycled to the mix tank that contains the feed to a $Na_2SO_4$ crystallizer in the IDA production process. Water is added to the solid to create a pumpable stream.

The instant invention will be better understood by referring to the following specific but non-limiting examples. It is understood that said invention is not limited by these procedures which are offered merely as illustrations; it is also understood that modifications can be made without departing from the spirit and scope of the invention.

EXAMPLE 1

1250 g of IDA liquor containing 6.4% IDA, 2.7% NTA, and 23.0% $Na_2SO_4$ was charged to a 1 liter crystallizer and equilibrated at 40° C. Five g of IDA seed crystals was added, then the mixture was linearly cooled at a rate of 5.8° C./hr. Five grams of $Na_2SO_4.10H_2O$ (Glauber's Salt) seed crystals was added at the saturation temperature of 27° C. At 13° C. about two thirds of the very heavy crystal slurry was centrifuged. The liquor was returned to the crystallizer and the mixture of this liquor and the remaining one third of the slurry was cooled to 5° C. The 5° C. slurry was stirred for 1 hour and then centrifuged. A total of 525 grams of liquor and 695 grams of wet cake was recovered. After air-drying (during which most of the water of crystallization was lost), the cake was found to contain 18.5% IDA, 0.7% NTA, and 67.8% $Na_2SO_4$; thus, 85% of the IDA and 90% of the $Na_2SO_4$ contained in the liquor were recovered in the cake.

EXAMPLE 2

The process of Example 1 was repeated, but 45 grams of 96% $H_2SO_4$ was added to the liquor to reduce the pH from the original 2.7 down to 2.0. The air-dried recovered cake contained 15.0% IDA and 6.1% NTA. The heavy contamination of the recovered solid demonstrated that this mode of operation was unsatisfactory.

EXAMPLE 3

The process of Example 2 was repeated except that after acidification to pH 2.0 the liquor was seeded with NTA, stirred 2 hours at 40° C., and then centrifuged to remove the crystallized NTA. The liquor was returned to the crystallizer, seeded with IDA, and cooled as described in Example 1. The NTA crop contained 83% NTA, 4.1% IDA, and 5.0% $Na_2SO_4$. The IDA crop was contaminated with 3.2% NTA which was considered unsatisfactory.

EXAMPLE 4

2500 grams of a new lot of IDA liquor containing 6.3% IDA, 3.0% NTA, and 23.3% $Na_2SO_4$ was charged to a 2 liter crystallizer and equilibrated at 40° C. 72 grams of 96% $H_2SO_4$ was added to pH 2.1, 10 grams of NTA seed was added, then the mixture was stirred for 2 hours. Additional $H_2SO_4$ was added as needed to maintain this pH. The precipitated NTA was separated on a centrifuge and washed. The liquor was returned to the crystallizer and re-equilibrated to 40° C. 82.8 grams of 50% NaOH was added to bring the liquor back to the original pH of 2.7. 10 grams of IDA seed was added and the batch was linearly program cooled to 5° C. over 6 hr. At 27° C. 5.0 grams of Glauber's Salt seed was added to initiate crystallization of Glauber's Salt. To maintain a workable slurry density, at both 25° C. and 15° C. about two thirds of the slurry was centrifuged, with the centrate being immediately returned to the crystallizer. The remaining slurry was centrifuged at 5° C. None of these crops was washed. The recoveries were:

|  | Grams | Analytical Data | | |
|---|---|---|---|---|
|  |  | % NTA | % IDA | % $Na_2SO_4$ |
| Air dried NTA crop | 63 | 95.0 | 4.4 | 0.4 |
| Mixed crops | 735 | 0.2 | 13.8 | 82.7 |
| Liquor | 1026 | 2.3 | 5.9 | 6.8 |

|  | % Recovered in Solids from Original Liquor | | |
|---|---|---|---|
|  | NTA | IDA | $Na_2SO_4$ |
| NTA Crop | 67% | | |

| | | |
|---|---|---|
| -continued | | |
| IDA/Glauber's Salt Mixed Crop | 58% | 89% |

What is claimed:

1. A process for separating iminodiacetic acid and sodium sulfate decahydrate from a starting aqueous solution comprising iminodiacetic acid and sodium sulfate, said process comprising the steps of:
   a. forming a slurry which is a solid mixture of iminodiacetic acid and sodium sulfate decahydrate, and a mother liquor; and
   b. separating the solid mixture from the mother liquor.

2. A process according to claim 1, wherein the slurry is formed by adjusting the temperature of the starting aqueous solution.

3. A process according to claim 1 comprising the further step of recycling at least a portion of the separated mother liquor to step a.

4. A process according to claim 1 further comprising adding iminodiacetic acid seed crystals to said starting aqueous solution prior to step a.

5. A process according to claim 4 wherein said seed crystals are added at about the saturation temperature of iminodiacetic acid in said solution.

6. A process according to claim 1 further comprising adding sodium sulfate decahydrate seed crystals during the formation of the slurry in step a.

7. A process according to claim 6 wherein the sodium sulfate decahydrate seed crystals are added at about the saturation temperature of sodium sulfate decahydrate in said starting aqueous solution.

8. A process according to claim 1, wherein said starting solution has a temperature of about 40° C. prior to step a.

9. A process according to claim 2, wherein the temperature is adjusted at a cooling rate of about 5.8° C./hr.

10. A process according to claim 2 wherein said solution is cooled to a temperature of about 5° C.

11. A process according to claim 1 wherein said separation is accomplished by centrifugation.

12. A process for separating iminodiacetic acid and sodium sulfate decahydrate from a starting aqueous solution comprising iminodiacetic acid and sodium sulfate, said process comprising the steps of:
   a. cooling said solution to a temperature effective for producing a solid mixture of iminodiacetic acid and sodium sulfate decahydrate, and a mother liquor; and
   b. separating the solid mixture from the mother liquor.

13. A process according to claim 12 comprising the further step of recycling at least a portion of the separated mother liquor to step a.

14. A process according to claim 12 further comprising adding iminodiacetic acid seed crystals to said starting aqueous solution prior to step a.

15. A process according to claim 14 wherein said seed crystals are added at about the saturation temperature of iminodiacetic acid in said solution.

16. A process according to claim 12 further comprising adding sodium sulfate decahydrate seed crystals during the cooling step.

17. A process according to claim 16 wherein the sodium sulfate decahydrate seed crystals are added at about the saturation temperature of sodium sulfate decahydrate in said starting aqueous solution.

18. A process according to claim 12, wherein said starting solution has a temperature of about 40° C. prior to the cooling step.

19. A process according to claim 12, wherein the cooling step is carried out at a cooling rate of about 5.8° C./hr.

20. A process according to claim 12 wherein said solution is cooled to a temperature of about 5° C.

21. A process according to claim 12 wherein said separation is accomplished by centrifugation.

22. A process for precipitating iminodiacetic acid and sodium sulfate decahydrate from a starting aqueous solution containing iminodiacetic acid and sodium sulfate, said solution having a temperature of about 40° C., said process comprising:
   a. cooling the solution to a temperature effective for precipitating iminodiacetic acid and sodium sulfate decahydrate;
   b. during said cooling step adding sodium sulfate decahydrate seed crystals at about the sodium sulfate decahydrate saturation temperature of said solution; and
   c. separating the precipitate.

23. A process according to claim 22 further comprising adding iminodiacetic acid seed crystals prior to step a.

24. A process according to claim 22 wherein said separation is accomplished by centrifugation.

25. A process for the continuous separation of iminodiacetic acid and sodium sulfate decahydrate from an aqueous solution comprising iminodiacetic acid and sodium sulfate, comprising:
   a. preparing a slurry of iminodiacetic acid, sodium sulfate decahydrate and liquor at about the temperature specified in step c;
   b. feeding said slurry into a crystallizer;
   c. feeding said aqueous solution comprising iminodiacetic acid and sodium sulfate into said slurry while cooling to maintain the temperature at a level effective for precipitating iminodiacetic acid and sodium sulfate decahydrate; and
   d. withdrawing said slurry and separating iminodiacetic acid and sodium sulfate decahydrate therefrom.

26. The process of claim 25 wherein the residence time of said solution in said crystallizer is about two hours.

27. The process of claim 25 further comprising recycling a portion of the liquor resulting from said separation to said crystallizer.

28. The process of claim 25 wherein the separation is accomplished by centrifugation.

29. The process of claim 25 wherein the aqueous solution in step c is fed into the slurry in the crystallizer.

30. The process of claim 25 wherein the aqueous solution in step c is fed into the slurry at a point prior to where said slurry enters said crystallizer.

31. In a process for recovering iminodiacetic acid from a starting aqueous solution consisting essentially of sodium sulfate, iminodiacetic acid, and water, said starting solution having a temperature above 33° C. and analyzing at least about 5% iminodiacetic acid, wherein said process comprises:
   a. forming a first slurry consisting essentially of a first crop of precipitated iminodiacetic acid and a first mother liquor by adjusting the pH of the starting solution to 1.5-3;

b. separating the first crop of precipitated iminodiacetic acid from the first mother liquor and recovering the separated iminodiacetic acid;
c. forming a second slurry having a temperature effective for preventing the precipitation of iminodiacetic acid therefrom and consisting essentially of precipitated sodium sulfate and a second mother liquor analyzing at least 5% dissolved iminodiacetic acid by evaporating water from the first mother liquor;
d. separating the precipitated sodium sulfate from the second mother liquor while maintaining the second slurry and the second mother liquor at a temperature effective for preventing iminodiacetic acid from precipitating therefrom;
e. forming a third slurry consisting essentially of a second crop of precipitated iminodiacetic acid and a third mother liquor by cooling the second mother liquor to 33°–40° C.; and
f. separating the second crop of precipitated iminodiacetic acid from the third mother liquor and recovering the separated iminodiacetic acid,
the improvement comprising:
g. cooling said third mother liquor to a temperature within a range effective for precipitating iminodiacetic acid and sodium sulfate decahydrate to form a fourth slurry, the fourth slurry comprising a mixture of precipitated iminodiacetic acid and sodium sulfate decahydrate and a fourth mother liquor; and
h. separating the precipitated iminodiacetic acid and sodium sulfate decahydrate from the fourth mother liquor.

32. The process of claim 31 comprising the further step of recycling at least a portion of said precipitated iminodiacetic acid and sodium sulfate decahydrate to step c.

33. The process of claim 31 comprising the further step of recycling at least a portion of said fourth mother liquor to step g.

34. The process of claim 31 further comprising adding iminodiacetic acid seed crystals to the third mother liquor prior to cooling said third mother liquor.

35. The process of claim 31 further comprising adding sodium sulfate decahydrate seed crystals during the cooling of said third mother liquor.

36. The process of claim 35 wherein the sodium sulfate decahydrate seed crystals are added at about the saturation temperature of sodium sulfate decahydrate in said third mother liquor.

37. A process for recovering iminodiacetic acid from a starting aqueous solution consisting essentially of sodium sulfate, iminodiacetic acid, and water, said starting solution having a temperature above 33° C. and analyzing at least about 5% iminodiacetic acid, wherein said process comprises:
a. forming a first slurry consisting essentially of a first crop of precipitated iminodiacetic acid and a first mother liquor by adjusting the pH of the starting solution to 1.5–3;
b. separating the first crop of precipitated iminodiacetic acid from the first mother liquor and recovering the separated iminodiacetic acid;
c. forming a second slurry having a temperature effective for preventing the precipitation of iminodiacetic acid therefrom and consisting essentially of precipitated sodium sulfate and a second mother liquor analyzing at least 5% dissolved iminodiacetic acid by evaporating water from the first mother liquor;
d. separating the precipitated sodium sulfate from the second mother liquor while maintaining the second slurry and the second mother liquor at a temperature effective for preventing iminodiacetic acid from precipitating therefrom;
e. forming a third slurry consisting essentially of a second crop of precipitated iminodiacetic acid and a third mother liquor by cooling the second mother liquor to 33°–40° C.;
f. separating the second crop of precipitated iminodiacetic acid from the third mother liquor and recovering the separated iminodiacetic acid,
g. preparing a fourth slurry of iminodiacetic acid, sodium sulfate decahydrate and a fourth mother liquor at about the temperature specified in step i;
h. feeding said fourth slurry into a continuous crystallizer;
i. continuously feeding said third mother liquor into said fourth slurry while cooling to maintain the temperature in a range effective for precipitating iminodiacetic acid and sodium sulfate decahydrate to form a fifth slurry, said fifth slurry comprising a mixture of precipitated iminodiacetic acid and sodium sulfate decahydrate and a fifth mother liquor; and
j. continuously separating the precipitated iminodiacetic acid and sodium sulfate decahydrate from the fourth mother liquor.

38. The process of claim 37 comprising the further step of recycling at least a portion of said separated iminodiacetic acid and sodium sulfate decahydrate to step c.

39. The process of claim 37 comprising the further step of continuously recycling at least a portion of said fifth mother liquor to step i.

40. The process of claim 37 further comprising adding iminodiacetic acid seed crystals to the third mother liquor prior to cooling said third mother liquor.

41. The process of claim 37 further comprising adding sodium sulfate decahydrate seed crystals during the cooling of said third mother liquor.

42. The process of claim 41 wherein the sodium sulfate decahydrate seed crystals are added at about the saturation temperature of sodium sulfate decahydrate in said third mother liquor.

43. A process for separating iminodiacetic acid and sodium sulfate decahydrate from a starting aqueous solution comprising iminodiacetic acid, sodium sulfate and nitrilotriacetic acid, said process comprising the steps of:
a. forming a first slurry consisting essentially of precipitated nitrilotriacetic acid and a first mother liquor;
b. separating the precipitated nitrilotriacetic acid from the first mother liquor;
c. forming a second slurry consisting essentially of precipitated iminodiacetic acid and sodium sulfate decahydrate and a second mother liquor; and
d. separating the precipitated iminodiacetic acid and sodium sulfate decahydrate from the second mother liquor.

44. The process of claim 43 wherein the first slurry is formed by adjusting the pH of the aqueous solution to a pH effective to precipitate nitrilotriacetic acid therefrom.

45. The process of claim 44 wherein the pH is adjusted to about 2.1.

46. The process of claim 44 wherein the pH is further adjusted after separation of the precipitated nitrilotriacetic acid to about the pH of the starting aqueous solution.

47. The process of claim 44 wherein the pH is further adjusted after separation of the precipitated nitrilotriacetic acid to about 2.6.

48. A process according to claim 43, wherein said second slurry is formed by adjusting the temperature of the first mother liquor.

49. A process according to claim 43 comprising the further step of recycling at least a portion of the separated second mother liquor to step c.

50. A process according to claim 43 further comprising adding sodium sulfate decahydrate seed crystals during the formation of the second slurry in step c.

51. A process according to claim 50 wherein the sodium sulfate decahydrate seed crystals are added at about the saturation temperature of sodium sulfate decahydrate in said second mother liquor.

52. A process according to claim 43, wherein said starting solution has a temperature of about 40° C. prior to step a.

53. A process according to claim 48, wherein the temperature is adjusted at a cooling rate of about 5.8° C./hr.

54. A process according to claim 48 wherein said first mother liquor is cooled to a temperature of about 5° C.

* * * * *